United States Patent
Ilev et al.

(10) Patent No.: US 10,302,528 B2
(45) Date of Patent: May 28, 2019

(54) CONFOCAL LASER METHOD AND DEVICE FOR MEASUREMENT OF OPTICAL PROPERTIES OF TORIC INTRAOCULAR LENSES

(71) Applicant: THE UNITED STATES OF AMERICA, as represented by the Secretary, Department of Health and Human Services, Washington, DC (US)

(72) Inventors: Ilko Kolev Ilev, Rockville, MD (US); Bennett Neave Walker, Silver Spring, MD (US); Robert Harold James, Gaithersburg, MD (US); Don Calogero, Montgomery Village, MD (US)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/545,018

(22) PCT Filed: Jan. 27, 2016

(86) PCT No.: PCT/US2016/015031
§ 371 (c)(1),
(2) Date: Jul. 20, 2017

(87) PCT Pub. No.: WO2016/123167
PCT Pub. Date: Aug. 4, 2016

(65) Prior Publication Data
US 2018/0275013 A1    Sep. 27, 2018

Related U.S. Application Data

(60) Provisional application No. 62/108,795, filed on Jan. 28, 2015.

(51) Int. Cl.
*G01M 11/02* (2006.01)
*A61F 2/16* (2006.01)

(52) U.S. Cl.
CPC ....... *G01M 11/0235* (2013.01); *A61F 2/1645* (2015.04); *G01M 11/0207* (2013.01); *G01M 11/0228* (2013.01)

(58) Field of Classification Search
CPC . G01M 11/0228; G01M 11/02; A61B 3/1005; A61F 2/16; A61F 2240/002;
(Continued)

(56) References Cited

U.S. PATENT DOCUMENTS 4,955,904 A * 9/1990 Atebara ................ A61F 2/1613
623/6.17
5,250,235 A * 10/1993 Cook ................ B29C 66/73921
156/272.8
(Continued)

FOREIGN PATENT DOCUMENTS

WO    WO 2008/080074        7/2008

OTHER PUBLICATIONS

International Search Report and Written Opinion for related International Application No. PCT/US2016/015031, 12 pages, dated May 6, 2016.

*Primary Examiner* — Sang H Nguyen
(74) *Attorney, Agent, or Firm* — Klarquist Sparkman, LLP (57) ABSTRACT

Described are systems, devices, and methods related to a confocal laser method (CLM) for accurately measuring dioptric powers and other critical optical properties of intraocular lenses (IOLs), such as toric IOLs. Described test results demonstrate that the described CLM systems and methods can be used to measure the spherical equivalent and cylinder powers of toric IOLs with high accuracy. Further-
(Continued)

more, some described systems include a rotating rectangular slit aperture that can be used for precise differentiation of the two focal planes and isolation of the two focal points, and thus, for accurate measurement of the anterior cylinder axis of toric IOLs.

20 Claims, 6 Drawing Sheets

(58) Field of Classification Search
CPC .. A61F 2009/00872; A61F 2009/00889; A61F 2009/00855; A61F 2009/00897; A61F 2009/00868
See application file for complete search history.

(56) References Cited

U.S. PATENT DOCUMENTS

| | | | |
|---|---|---|---|
| 5,512,966 A * | 4/1996 | Snook | A61B 3/1005 351/205 |
| 5,926,252 A | 7/1999 | Reyburn | |
| 9,211,061 B2 * | 12/2015 | Kasthurirangan | A61B 3/0025 |
| 2004/0246440 A1 * | 12/2004 | Andino | A61B 3/0025 351/159.74 |
| 2006/0238711 A1 * | 10/2006 | Kitajima | A61B 3/135 351/214 |
| 2007/0115455 A1 * | 5/2007 | Ilev | G01P 5/20 356/28 |
| 2007/0236701 A1 * | 10/2007 | Neal | A61B 3/1005 356/512 |
| 2008/0278712 A1 * | 11/2008 | Ilev | G01M 11/0228 356/125 |
| 2009/0225409 A1 * | 9/2009 | Ilev | G02B 21/0032 359/385 |
| 2010/0134760 A1 * | 6/2010 | Salvati | A61B 3/0025 351/206 |
| 2010/0208199 A1 | 8/2010 | Levis et al. | |
| 2011/0170059 A1 * | 7/2011 | Ehrmann | G09B 23/22 351/205 |
| 2011/0237999 A1 * | 9/2011 | Muller | A61F 9/008 604/20 |
| 2011/0279821 A1 * | 11/2011 | Brennan | A61B 3/102 356/479 |
| 2014/0232986 A1 | 8/2014 | Gerten | |
| 2015/0216404 A1 * | 8/2015 | Zhao | A61B 3/0025 356/124 |
| 2016/0227998 A1 * | 8/2016 | Schmoll | A61B 3/12 |

* cited by examiner

| | MANUFACTURER | | | CONVENTIONAL INSTRUMENT | | | | | | CLM | | | | |
|---|---|---|---|---|---|---|---|---|---|---|---|---|---|---|
| | LABELED MEASUREMENT | | TESTED MEASUREMENT | | | | | | | | | | | |
| IOL # | SE | CYLINDER | SE ($SE_i$) | CYLINDER ($C_i$) | $SE_{AVG}$ | STD (% ERROR) | $C_{AVG}$ | STD (% ERROR) | MEASURED & ADJUSTED ($SE_{CLM}$) | STD | $SE_i$-$SE_{CLM}$ | MEASURED & ADJUSTED ($C_{CLM}$) | STD | $C_i$-$C_{CLM}$ (%ERROR) |
| 1 | 5 | 1.5 | 5.04 | 1.45 | 4.23 | 0.002 (16.1%) | 1.54 | 0.001 (6.2%) | 5.16 | 0.016 | -0.12 (2.34%) | 1.56 | 0.051 | -0.12 (7.75%) |
| 2 | 5 | 2.25 | 5.05 | 2.24 | 4.80 | 0.030 (4.95%) | 2.26 | 0.034 (0.89%) | 5.17 | 0.029 | -0.12 (2.46%) | 2.31 | 0.071 | -0.08 (3.19%) |
| 3 | 5 | 3.0 | 5.04 | 2.98 | 4.71 | 0.031 (6.55%) | 2.88 | 0.026 (3.35%) | 5.16 | 0.018 | -0.15 (2.42%) | 3.05 | 0.051 | -0.09 (2.25%) |
| 4 | 5 | 4.0 | 5.04 | 4.11 | 4.25 | 0.002 (15.6%) | 4.136 | 0.002 (0.63%) | 5.24 | 0.017 | -0.2 (3.90%) | 3.98 | 0.042 | 0.11 (3.15%) |
| 5 | 20 | 1.5 | 19.95 | 1.48 | 20.05 | 0.014 (0.5%) | 1.72 | 0.003 (16.22%) | 20.01 | 0.082 | -0.06 (0.29%) | 1.47 | 0.002 | 0.01 (0.49%) |
| 6 | 20 | 2.25 | 20.00 | 2.21 | 20.00 | 0.018 (0%) | 2.27 | 0.001 (2.71%) | 20.30 | 0.012 | -0.03 (1.59%) | 2.22 | 0.006 | -0.02 (0.64%) |
| 7 | 20 | 3.0 | 19.94 | 2.90 | 19.70 | 0.012 (1.2%) | 2.95 | 0.023 (1.72%) | 20.30 | 0.012 | -0.36 (1.82%) | 3.18 | 0.008 | -0.29 (9.54%) |
| 8 | 20 | 4.0 | 20.01 | 3.93 | 19.85 | 0.016 (0.79%) | 3.99 | 0.007 (1.53%) | 20.13 | 0.027 | -0.12 (0.57%) | 4.07 | 0.004 | -0.15 (3.65%) |
| 9 | 34 | 1.5 | 34.06 | 1.55 | 35.33 | 0.003 (3.73%) | 1.54 | 0.004 (0.64%) | 34.15 | 0.03 | -0.09 (0.25%) | 1.53 | 0.006 | 0.02 (1.54%) |
| 10 | 34 | 2.25 | 33.89 | 2.26 | 35.026 | 0.015 (3.35%) | 2.39 | 0.002 (5.75%) | 34.11 | 0.033 | -0.22 (0.64%) | 2.30 | 0.048 | -0.04 (1.96%) |
| 11 | 34 | 3.0 | 33.82 | 2.26 | 35.00 | 0.020 (3.49%) | 3.27 | 0.003 (10.47%) | 33.95 | 0.021 | -0.13 (0.37%) | 3.03 | 0.04 | -0.07 (2.26%) |
| 12 | 34 | 4.0 | 33.69 | 4.01 | 34.38 | 0.009 (2.05%) | 4.10 | 0.004 (2.24%) | 33.92 | 0.055 | -0.23 (2.05%) | 4.04 | 0.019 | -0.04 (0.76%) |

FIG. 4

| IOL # | TRIAL 1 (T$_1$) | | TRIAL 2 (T$_2$) | | |T$_1$-T$_2$| | |
|---|---|---|---|---|---|---|
| | SE | CYLINDER POWER | SE | CYLINDER POWER | SE | CYLINDER POWER |
| 6 | 20.24 | 2.22 | 20.28 | 2.29 | 0.04 | 0.07 |
| 10 | 34.02 | 2.33 | 33.94 | 2.29 | 0.08 | 0.04 |

FIG. 5

| IOL # | MEASURED AXIS (°) |
|---|---|
| 1 | 92 ±4 |
| 2 | 90 ±2 |
| 3 | 92 ±2 |
| 4 | 90 ±4 |
| 5 | 86 ±4 |
| 6 | 88 ±2 |
| 7 | 90 ±4 |
| 8 | 92 ±2 |
| 9 | 88 ±4 |
| 10 | 86 ±6 |
| 11 | 92 ±2 |
| 12 | 84 ±6 |

FIG. 6

CONFOCAL LASER METHOD AND DEVICE FOR MEASUREMENT OF OPTICAL PROPERTIES OF TORIC INTRAOCULAR LENSES

CROSS-REFERENCE TO RELATED APPLICATIONS

This application is the U.S. National Stage of International Application No. PCT/US2016/015031, filed Jan. 27, 2016, which was published in English under PCT Article 21(2), and which claims the benefit of U.S. Provisional Application No. 62/108,795 filed Jan. 28, 2015, which is incorporated by reference herein in its entirety.

FIELD

This application is related to the measurement of optical properties of intraocular lenses.

BACKGROUND

Intraocular lens (IOL) implantation to treat cataracts and aphakia is one of the most common surgical procedures performed, with an estimated 3 million surgeries per year in the United States and millions more worldwide. As a result, the industry is rapidly growing, with new IOL designs and materials emerging each year. Since the emergence of the simple glass monofocal IOLs, more flexible materials have been introduced having more complex optical capabilities, such as toric and multifocal lenses.

To accommodate this constantly evolving field, the development and investigation of innovative standard test methods for precise and objective evaluation of IOL optical properties is important. To effectively accomplish this goal, critical optical properties that affect the safety and efficacy of IOLs need to be identified and targeted. These properties include dioptric powers, reflected glare, imaging quality, and light glistenings.

Furthermore, environmental parameters that influence optical properties need to be quantitatively evaluated (e.g. conical temperature, contaminants, properties of surrounding media, and exposed light). Research is ongoing to systematically assess how changes in the environmental parameters influence critical optical properties. As an example, changes in IOL surface temperatures can result in significant changes in dioptric powers, astigmatism, and spherical aberrations. Additionally, changes in environmental parameters are largely dependent on the IOL designs themselves. For example, the angular edge design of some IOLs has been found to produce unwanted glare.

Approximately 30% of patients in need of cataract surgery also have more than 1.50 D of corneal or refractive astigmatism. Toric IOLs were introduced to correct these corneal astigmatisms and provide different optical properties in comparison with the more basic spherical IOLs. The toric IOLs produce two dioptric powers (spherical equivalent, SE; and cylinder, C) by including an asymmetrical lens aligned orthogonally to a spherical lens. The cylinder power is lower than the spherical equivalent and is designed to reduce mild to moderate astigmatism. The additional unique dioptric power properties introduced by toric IOLs means that additional requirements are needed to properly evaluate their safety and efficacy. For example, to accommodate the new plane of focus of toric IOLs, tick marks are used to indicate the anterior cylinder axis. The accuracy of aligning the tick marks during implantation can significantly influence the efficacy of the IOL and as a result, high precision is required. Occasionally the IOL will need to be re-aligned a few weeks after the primary implantation.

SUMMARY

The introduction of new optical properties from the evolving IOL designs requires the development of new methods to accurately evaluate the efficacy and safety of such lenses as well as to improve the testing precision and to accommodate new areas of interest. The confocal laser method (CLM) can be used to measure IOL dioptric powers with improved precision (e.g., ≤1 µm of focal length measurement), repeatability (e.g., <0.05 D), accessible dioptric ranges (e.g., 0 to ±36.0 D), and accommodation for evolving lens designs. Through the principles of confocal microscopy, the CLM uses a fiber-optic confocal laser design to quantitatively measure the back focal length of IOLs, and ultimately their dioptric powers. The CLM is effective for measuring monofocal IOLs, and is also effective for measuring other IOL types (e.g. toric, multifocal, and accommodating).

This disclosure describes the development and implementation of a new CLM testing system that is effective for precise quantitative evaluation of critical optical properties unique to toric IOLs, such as spherical equivalent (SE) and cylinder (C) dioptric powers, and anterior cylinder axis. Results obtained from testing various toric IOL samples using the disclosed systems and methods demonstrate the utility of the CLM for measuring these IOL optical properties with high accuracy and repeatability. Disclosed CLM systems and methods can accurately and precisely measure the SE and C powers of toric IOLs, even for IOLs with low cylinder powers (where the two focal points are close to each other). In addition, while using the disclosed CLM systems and methods, it is possible to control and simulate environmental parameters that are known to influence optical properties in order to conform to the ISO Standard and determine the influence of each parameter on various optical property measurements.

In addition, some disclosed CLM systems include a rotating rectangular slit aperture that allows for the two planes of focus to be isolated and measured between one another as well as with respect to the axial tick marks on a toric IOLs, enabling the CLM system to be used to verify the accuracy of the toric IOL tick marks.

The foregoing and other objects, features, and advantages of the disclosed technology will become more apparent from the following detailed description, which proceeds with reference to the accompanying figures.

BRIEF DESCRIPTION OF THE DRAWINGS

FIG. 4 is a table showing spherical equivalent (SE) and cylinder (C) power values and measurement error values for various IOLs, as provided by IOL manufactures (left columns), as measured using conventional instruments (center columns), and as measured using the disclosed CLM systems (right columns). Standard deviation (STD) is the observed error from measurement to measurement while "% Error" is the calculated error compared to the manufacturer provided values, based on Equation 1 above provided herein. The column "Measured & Adjusted" refers to the accepted calculation required to convert the measured spherical power (S) to the labeled spherical equivalent power (SE).

DETAILED DESCRIPTION

Described herein are systems, devices, and methods related to the confocal laser method (CLM) for accurately measuring dioptric powers and other critical optical properties of intraocular lenses (IOLs), such as toric IOLs. A toric lens is a lens with different optical power and focal length in two orientations perpendicular to each other. One of the lens surfaces can be shaped like a "cap" from a torus, while the other lens surface can be spherical. The lens surface that is shaped like a "cap" from a torus can have one curvature defined by the outer circumference of the torus from which the cap is "cut", with a radius of curvature equal to the radial distance from the center of the torus to the outer circumference of the torus (i.e., the major radius "R" plus the minor radius "r"), and a second curvature perpendicular to the first with a radius of curvature equal to the radius of the tube of the torus (i.e., the minor radius "r").

Herein is described the development and implementation of an innovative CLM system for precise evaluation of critical optical properties of toric IOLs. Described test results demonstrate that the described CLM systems and methods can be used to measure the spherical equivalent (SE) and cylinder (C) powers of toric IOLs with high accuracy (e.g., ≤1 μm in spatially locating focal points and focal length measurement). Furthermore, some described systems include a rotating rectangular slit aperture that can be used for precise differentiation of the two focal planes and isolation of the two focal points, and thus, for accurate measurement of the anterior cylinder axis of toric IOLs.

Exemplary Testing Procedures

Figure 1A:
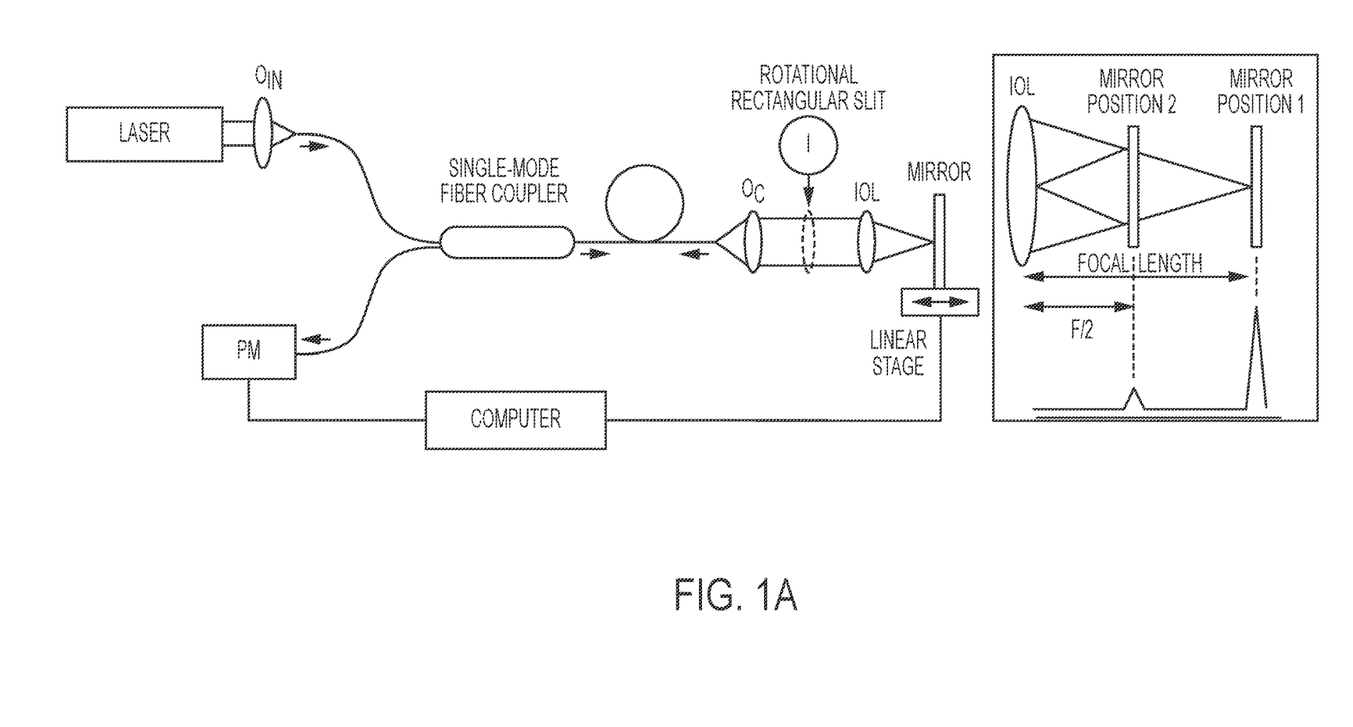
FIG. 1A is a schematic of a confocal laser method (CLM) system, which can be used to determine optical properties of toric IOLs. The schematic on right illustrates how the focal length and half-focal length (F/2) are determined using the system illustrated on the left.

The optical properties of toric IOLs can be measured using a CLM system such as the exemplary system illustrated in FIG. 1A. In one example CLM system, a 543-nm (±1 nm), low-noise laser is coupled into a 1×2, 633-nm, single-mode fiber coupler using a 10× objective lens ("$O_{in}$" in FIG. 1A). The laser output beam from the single-mode fiber coupler is then collimated with a 10× infinity corrected objective lens ("$O_C$" in FIG. 1A) on a cage system aligned with an IOL receiver configured to mount a toric IOL or other type of IOL in a fixed position aligned with the objective lens $O_C$.

In other embodiments of the described CLM testing system, different types of laser and/or light sources can be used, any suitable fiber-optic coupler can be used, and/or objective lens having different powers can be used to produce a collimated Gaussian laser beam directed at an IOL test sample mounted in the IOL receiver.

Figure 1B:
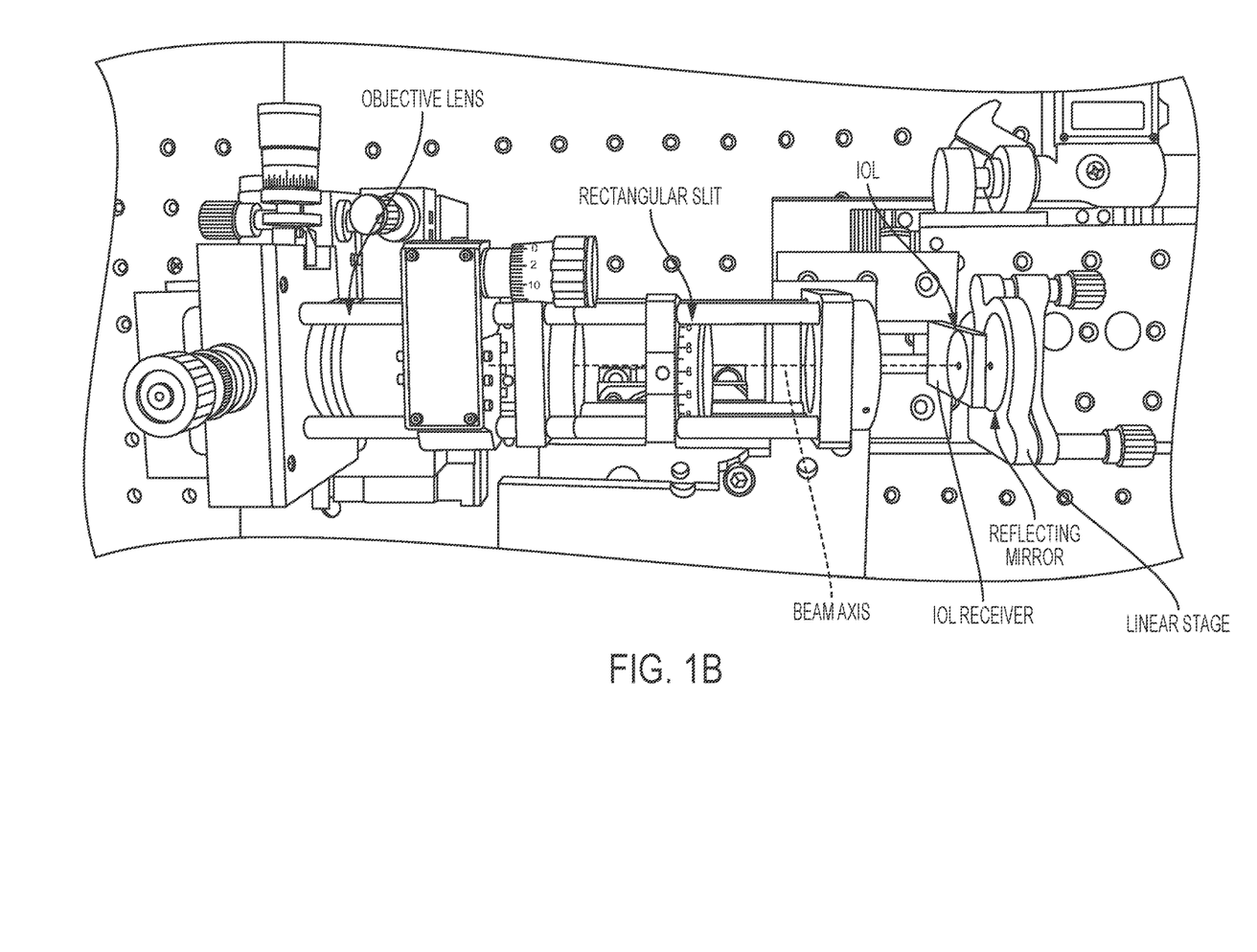
FIG. 1B shows an exemplary embodiment of the CLM system of FIG. 1, with the dashed line illustrating the laser beam path.

Employing confocal microscopy principles, the collimated Gaussian laser beam can be focused by an IOL test sample ("IOL" in FIG. 1A) and then back-reflected by a total reflectance mirror ("Mirror" in FIG. 1A) mounted on a motorized and automated linear stage. The reflected light then passes back through the IOL and the objective lens and is refocused into the fiber coupler to an optical power measuring device, or power meter, ("PM" in FIG. 1A), where the optical properties of the received light can be measured by a power meter. The axial position and motion of the back-reflectance mirror can be accurately integrated with the optical power meter measurements using custom software and a computing system that is in signal communication with the power meter and to the linear stage of the mirror. An exemplary CLM testing system is depicted in FIG. 1B, where the green dashed line illustrates the path of the test laser beam.

The IOL dioptric powers can be determined by measuring the back focal length, $F_{BFL}$, which can be determined by doubling the distance between the peaks of the spherical equivalent, SE, dioptric power profile and its corresponding half-focal profile, as depicted in the schematic at the right of FIG. 1A. The spherical dioptric power, S, can then be calculated from the measured back focal length using the following equation:

$$S = n_{med}/[F_{BFL}/(1-t(n_{IOL}-n_{med})/(n_{IOL} \times R))] \quad (1)$$

where, $n_{med}$ is the refractive index in medium, $n_{IOL}$ is the refractive index of the IOL, t is the IOL thickness, and R is the front surface radius of curvature of the IOL.

The focal point profile of the dioptric powers can be determined to be paraxial, enabling accurate differentiation between the often closely aligned spherical equivalent and cylinder powers. In addition, dioptric power measurements can be compared with IOL manufacturer measurements as well as measurements obtained using conventional measurement devices, such as a Crystal Wave Intraocular Lens Aberrometer available from Lumetrics Inc. of Rochester, N.Y.

Testing using the described CLM system and methods was performed on various exemplary one-piece biconvex, aspheric toric IOLs having varying SE and C powers, with their optical properties being studied in similar environmental conditions. The tested toric IOLs were fabricated from hydrophobic acrylic material and were measured in air at room temperature (approximately 20.0° C.). In other embodiments, any type of IOLs can be used and tested.

Figure 1C:
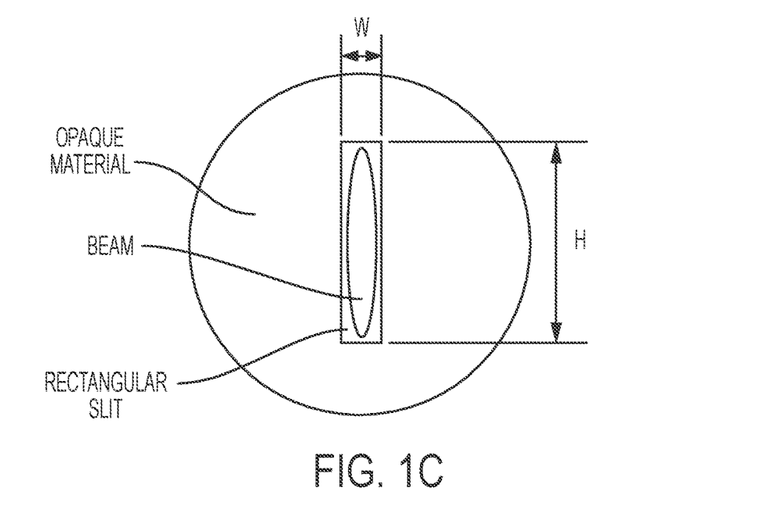
FIG. 1C illustrates a rotational rectangular slit aperture used in the CLM system of FIGS. 1A and 1B for precise evaluation of the anterior cylinder axis of toric IOLs. The beam spot within the slit aperture illustrates the test laser beam profile.

The CLM system shown in FIGS. 1A and 1B can also include a measurement tool for precise evaluation of the anterior cylinder axis of toric IOLs. For example, the measurement tool can include a rotational slit aperture, such as a rectangular slit aperture as shown in FIG. 1C. The rotational slit aperture can be integrated onto the cage system shown in FIG. 1B. The rectangular slit width ("W" in FIG. 1C) can be selected to be equal to or larger than the width of the test focused laser beam, such as in a range of about 0.5 mm to about 1.0 mm. The slit height ("H" in FIG.

Figure 3:
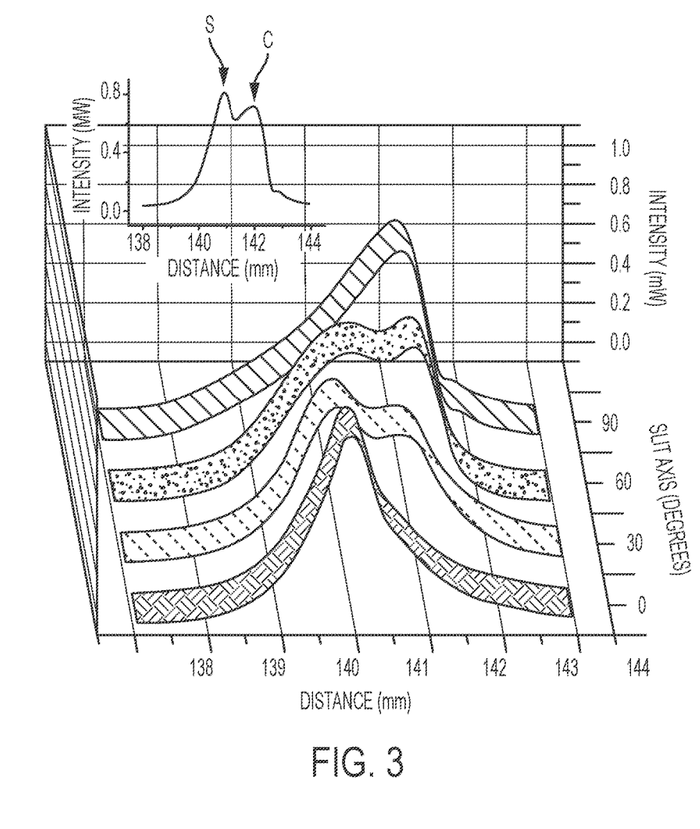
FIG. 3 is a three dimensional graph depicting the peak shift as the rectangular slit is rotated from aligning with the IOL tick marks to its aspheric surface. 0° is designated as the location where the magnitude of spherical power peak is greatest. The inset shows a graph of spherical equivalent SE (S) and cylinder (C) power peaks when no rectangular slit is present.

1C) can be between about 1.0 mm and about 5.0 mm, and can be for example about 3 mm in accordance with standard requirements for IOL dioptric power measurement. By rotating the rectangular slit aperture about the laser beam axis, the observed focal point shifts between the spherical equivalent power and the cylinder power, as illustrated in FIG. 3. Employing this approach, precise differentiation of the two focal planes and isolation of the two focal points can be achieved, and thus, the anterior cylinder axis orientation can be determined at high accuracy, such as to within of a few degrees or less (see exemplary results shown in FIG. 6).

Exemplary Testing Results and Analysis

Figure 2:
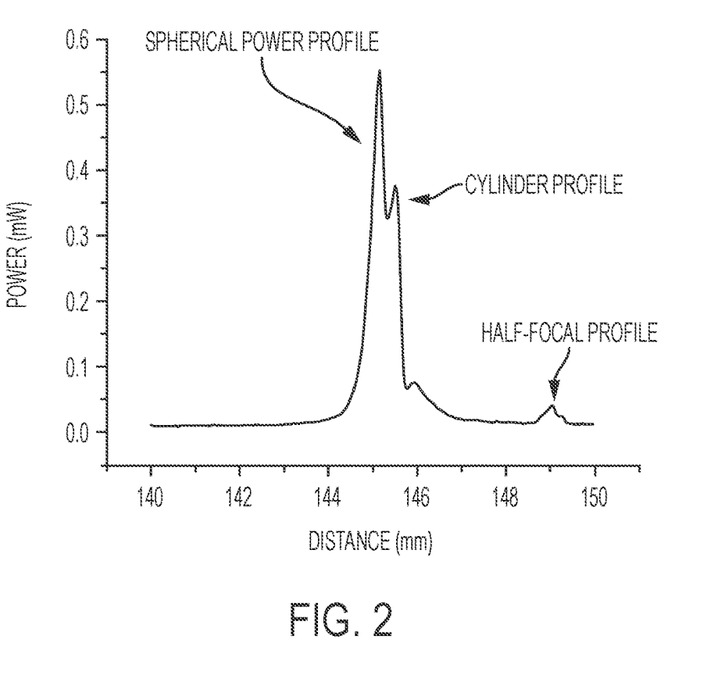
FIG. 2 is graph illustrating a power profile of an exemplary IOL as measured using the CLM system of FIG. 1.

The described CLM system and methods were used to measure the focal point profiles of the spherical, cylinder, and half-focal point for several exemplary toric IOLs. The results for one exemplary toric IOL are shown in FIG. 2. By coordinating the optical power sensor with a mechanical linear stage, for example at 1-μm step sizes (other step sizes are possible), the distance between the focal points can be accurately measured and translated into dioptric powers. In addition, due to its paraxial nature, the resulting Gaussian profile enables highly accurate and repeatable measurements.

In the case of toric IOLs, the spherical equivalent and cylinder powers can be determined from the calculated dioptric powers, S, based on measurements of the spherical and cylinder powers. The labeled cylinder power (C) is the difference between the powers of these two measurements. The labeled spherical equivalent power (SE) is determined by the following equation:

$$SE = S + 0.5C \quad (2)$$

In one study, 12 different toric IOLs of varying labeled spherical equivalent powers (5.0 D, 20.0 D, and 34.0 D) and cylinder powers (1.5 D, 2.25 D, 3.00 D, and 4.00 D) were measured with the described CLM system and methods. As shown in FIG. 4, the measured powers obtained using the CLM system (labeled "CLM" in FIG. 4) were compared with powers provided by the IOL manufacturer (labeled "Manufacturer" in FIG. 4) as well as powers obtained from a Wavefront aberrometer (labeled "Conventional Instrument" in FIG. 4). The results from the 12 tested IOLs are summarized in the 12 corresponding rows of FIG. 4. The "Manufacturer" section gives the labeled powers for both the SE and C of the toric IOL as well as their actual measured powers provided by the manufacturer ($SE_i$ and $C_i$. The "Conventional Instrument" section provides the average SE and C measurements from the commercial aberrometer along with the corresponding standard deviation and percent error when compared to the manufacturers' measurements (labeled as % Error). The "CLM" section provides the optical property measurements using the disclosed CLM system and methods, including measured dioptric powers and standard deviation (determined by three separate measurements), as well as the difference when compared to the manufacturers' measurements ($SE_i$-$SE_{CLM}$ and $C_i$-$C_{CLM}$) and the corresponding percent error.

Results from FIG. 4 show that the spherical equivalent measurements obtained from the disclosed CLM system and methods compare well with the manufacturers' labeled power for the middle to high powered IOLs (0.25%-2.05% error). The 5.0 D IOLs result in larger errors (2.34%-3.90%), which are still within the accepted ISO tolerance range.

Figure 5:
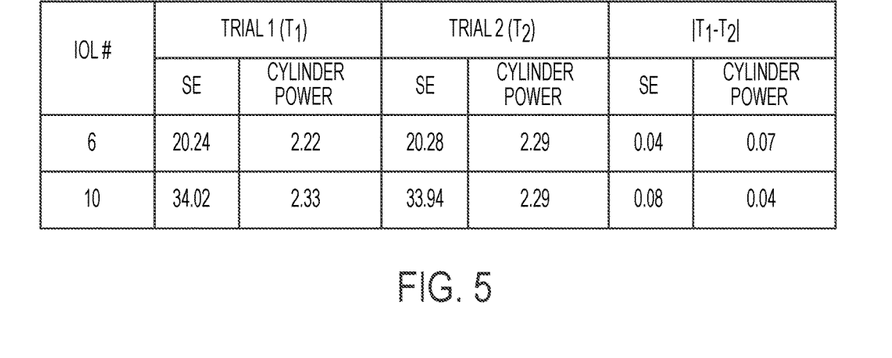
FIG. 5 is a table showing measured differences between two trial measurements using the CLM system after complete realignment of the CLM platform.

The standard deviation for the CLM results is relatively low, between 0.002 and 0.082 D (shown in FIG. 4), indicating good repeatability and reproducibility. However, these deviations are observed from measurements which utilized the same alignment procedures and therefore only show deviation due to mechanical and program errors. To more accurately analyze the reproducibility of the disclosed CLM methods, the platform was dismantled and realigned between experiments for IOLs #6 and #10. The results of this more robust reproducibility study are shown in FIG. 5 showing |T1-T2| measurement differences of 0.04 D and 0.08 D for SE as well as 0.07 D and 0.04 D for C, well within the ISO tolerance range. These results indicate that the disclosed CLM system and methods provide a highly accurate and reproducible way to measure IOL optical powers.

The axes of the two planes of some IOLs are manufactured to lie orthogonally from each other with tick marks identifying the axis of the lower powered lens. Proper alignment of the lens with the corneal plane can be difficult and sometimes results in post-surgical realignment. The accuracy of the tick marks in relation to the meridian axis is important for proper alignment, as well as the orthogonality of the two lens planes. By integrating a rotating rectangular slit, such as the example shown in FIG. 1C, into the CLM system cage platform, as shown in FIGS. 1A and 1B, the precise location of the two planes can be determined preclinically to a high degree of accuracy (e.g., to within a few degrees, and/or to within one degree), and can be further significantly improved by incorporating automated controls. The two lens planes can be determined by measuring the angle required to shift the focal point profiles from the spherical power to the cylinder power.

A power profile for IOL #7 is shown as an example in FIG. 3, where the focal point profile clearly shifts from the spherical power (0°) to the cylinder power (90°), while showing profiles in between the 90° rotation. The inset in FIG. 3 shows how the focal point profiles look when no rectangular slit is included in the system.

Figure 6:
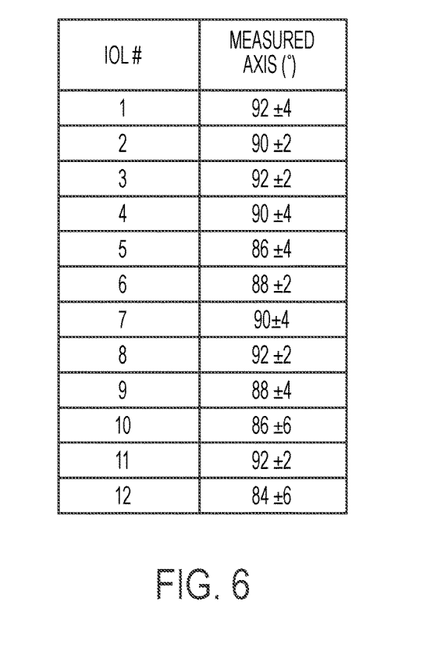
FIG. 6 is a table showing measured optical plane orthogonality of several exemplary toric IOLs using a rotational rectangular slit.

FIG. 3 illustrates how a CLM system, with the rectangular slit, can be used to very precisely determine the accuracy of the tick marks as well as potentially determining the orthogonality of the two lens planes. In addition, the slit can be used to improve the accuracy of the CLM system by isolating each lens plane so that only one plane is observed and measured for each experiment. FIG. 6 shows the measured axis of the 12 toric IOLs represented in FIG. 4. Measurements can be determined with a rotational mount including tick mark indicators at close intervals, such as every 2° or smaller intervals, in order to provide a desired level of accuracy. The rotational distance needed to travel between optical peaks was measured three separate times, providing the uncertainty units in the table of FIG. 6. From this study, the orthogonality of all the tested IOLs were found within error.

By improving the accuracy of dioptric power measurements, using the disclosed CLM systems and methods, more precise IOLs can be manufactured that are better personalized to individual patients. Furthermore, employing the disclosed testing methods, preclinical evaluation of toric IOL tick mark accuracies can ensure the effectiveness of the toric IOL before implantation occurs. In addition, by evaluating the accuracy of the tick marks on a toric IOL, the lens can be more precisely positioned during surgery so the patient will be less likely to need post-operative adjustments and have improved astigmatism correction capabilities.

In some embodiments, relevant environmental conditions such as ambient temperature can be controlled, such as by incorporating a temperature controlled bath in the system.

In some embodiments, CLM systems can be capable of not only evaluating critical optical properties of toric IOLs, but can also be capable of evaluating critical optical properties of monofocal, multifocal, accommodating, and/or future IOL as well as contact lens designs due to the adaptable confocal microscopy principles. The disclosed technology can also be used to measure/determine optical properties of contact lenses in a similar manner as for IOLs.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Integers, characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims.

The invention claimed is:

1. A system for testing optical properties of a toric intraocular lens (IOL), the system comprising:
an objective lens;
an IOL receiver for mounting a toric IOL to be measured in fixed axial alignment with the objective lens;
a total reflectance mirror positioned in axial alignment with the objective lens and on an opposite side of the IOL receiver from the objective lens, the mirror being linearly adjustable relative to the IOL receiver to adjust an axial distance between the mirror and a toric IOL mounted in the IOL receiver; and
a rotational slit aperture positioned between the objective lens and the IOL receiver, the slit aperture being rotationally adjustable relative to the IOL receiver to adjust a rotational orientation of the slit aperture about an axis passing through the objective lens and a toric IOL mounted in the IOL receiver;
wherein a test laser beam passing through a toric IOL mounted in the IOL receiver is limited by the slit aperture to a plane corresponding to the rotational orientation of the slit aperture; and
wherein the slit aperture allows two planes of focus of a toric IOL mounted in the IOL receiver to be isolated and measured separately from one another.

2. The system of claim 1, wherein the system is capable of measuring a spherical equivalent dioptric power and a cylindrical dioptric power of a toric IOL mounted in the IOL receiver.

3. The system of claim 1, wherein the slit aperture comprises a rectangular slit.

4. The system of claim 1, wherein the slit aperture allows two planes of focus of a toric IOL mounted in the IOL receiver to be isolated and measured with respect to markings on the toric IOL that indicate an anterior cylinder axis on the toric IOL.

5. The system of claim 1, further comprising a fiber-optic coupler configured to direct light from a light source toward the objective lens, and configured to direct light from the objective lens to an optical power measuring device.

6. The system of claim 5, further comprising a controller coupled to the optical power measuring device and coupled to an actuator for the mirror, the controller configured to control axial movement of the mirror and configured to correlate data obtained by the optical power measuring device with the axial position of the mirror to evaluate a toric IOL mounted in the IOL receiver.

7. A method for testing optical properties of a toric intraocular lens (IOLs), the method comprising:
positioning a toric IOL in axial alignment between a rotational slit aperture and an axially adjustable total reflectance mirror;
with the slit aperture in a first rotational orientation, directing a collimated laser beam toward the slit aperture such that a portion of the laser beam passes through the slit aperture and through the toric IOL to the mirror, then reflects off the mirror back through the toric IOL and the slit aperture to an optical power measuring device;
adjusting the slit aperture to a second rotational orientation; and
with the slit aperture in the second rotational orientation, directing a collimated laser beam toward the slit aperture such that a portion of the laser beam passes through the slit aperture and through the toric IOL to the mirror, then reflects off the mirror back through the toric IOL and the slit aperture to an optical power measuring device.

8. The method of claim 7, further comprising determining an anterior cylinder axis of the toric IOL based measurements obtained from the light received by the optical power measuring device with the slit aperture in the first rotational orientation and in the second rotational orientation.

9. The method of claim 8, further comprising evaluating the accuracy of markers on the toric IOL that indicate the anterior cylinder axis of the toric IOL based on a comparison of the markers with the determined location of the anterior cylinder axis of the toric IOL.

10. The method of claim 7, further comprising adjusting the axial position of the mirror while evaluating light received by the optical power measuring device to determine a spherical equivalent power of the toric IOL and determine a cylindrical power of the toric IOL.

11. The method of claim 10, where determining the spherical equivalent power of the toric IOL comprises determining a spherical power and the cylindrical power of the toric IOL and calculating the spherical equivalent power as the sum of the spherical power plus half of the cylindrical power.

12. The method of claim 7, wherein the spherical power, cylindrical power, and half-focal point of the toric IOL are determined by adjusting the axial position of the mirror while determining corresponding focal points of the toric IOL using the optical power measuring device.

13. The method of claim 7, wherein the spherical power of the toric IOL is calculated using the formula:

$$S = n_{med}[F_{BFL}/(1 - t(n_{IOL} - n_{med})/(n_{IOL} \times R))]$$

where S is the spherical power, $n_{med}$ is a refractive index in medium, $n_{IOL}$ is a refractive index of the IOL, t is a thickness of the IOL, and R is a front surface radius of curvature of the IOL.

14. The method of claim 7, wherein a first plane of focus of the toric IOL is isolated with the slit aperture in the first rotational position, and a second plane of focus of the toric IOL is isolated with the slit aperture in the second rotational position.

15. The method of claim 7, wherein a spherical power focal point of the toric IOL can be determined with the slit aperture in the first rotational position and a cylindrical power focal point of the toric IOL can be determined with the slit aperture in the second rotational position.

16. The method of claim 7, further comprising evaluating an orthogonality between two optical planes of focus of the toric IOL by measuring a rotational distance of the slit aperture between the first rotational position and the second rotational position.

17. A method comprising:
evaluating optical properties of a toric intraocular lens (IOL) using the method of claim 7; and
based on the evaluated optical properties, determining a desired orientation of the IOL for implantation of the IOL in a patient's eye.

18. The method of claim 7, further comprising controlling an ambient temperature around the toric IOL or a temperature of the toric IOL while optical properties of the toric IOL are being evaluated.

19. The method of claim 7, further comprising rotationally adjusting the slit aperture to a plurality of positions in increments of less than 2°.

20. A system for testing optical properties of a toric intraocular lens (IOL), the system comprising:
an objective lens;
an IOL receiver for mounting a toric IOL to be measured in fixed axial alignment with the objective lens;
a total reflectance mirror positioned in axial alignment with the objective lens and on an opposite side of the IOL receiver from the objective lens, the mirror being linearly adjustable relative to the IOL receiver to adjust an axial distance between the mirror and a toric IOL mounted in the IOL receiver; and
a rotational slit aperture positioned between the objective lens and the IOL receiver, the slit aperture being rotationally adjustable relative to the IOL receiver to adjust a rotational orientation of the slit aperture about an axis passing through the objective lens and a toric IOL mounted in the IOL receiver;
wherein a test laser beam passing through a toric IOL mounted in the IOL receiver is limited by the slit aperture to a plane corresponding to the rotational orientation of the slit aperture;
wherein the system further comprises a fiber-optic coupler configured to direct light from a light source toward the objective lens, and configured to direct light from the objective lens to an optical power measuring device; and
wherein the system further comprises a controller coupled to the optical power measuring device and coupled to an actuator for the mirror, the controller configured to control axial movement of the mirror and configured to correlate data obtained by the optical power measuring device with the axial position of the mirror to evaluate a toric IOL mounted in the IOL receiver.

* * * * *